(12) United States Patent
Gray et al.

(10) Patent No.: US 7,371,918 B2
(45) Date of Patent: May 13, 2008

(54) ALKYLATION PROCESS WITH SETTLER EFFLUENT RECYCLE

(75) Inventors: Robert M. Gray, Bartlesville, OK (US); Keith W. Hovis, Stillwater, OK (US)

(73) Assignee: UOP LLC, Des Plaines, IL (US)

( * ) Notice: Subject to any disclaimer, the term of this patent is extended or adjusted under 35 U.S.C. 154(b) by 147 days.

(21) Appl. No.: 11/012,811

(22) Filed: Dec. 15, 2004

(65) Prior Publication Data

US 2006/0129014 A1 Jun. 15, 2006

(51) Int. Cl.
*C07C 2/62* (2006.01)
*C07C 2/56* (2006.01)

(52) U.S. Cl. ............... 585/716; 585/714; 585/723; 585/724

(58) Field of Classification Search ............ 585/714, 585/716, 723, 724
See application file for complete search history.

(56) References Cited

U.S. PATENT DOCUMENTS

| | | | |
|---|---|---|---|
| 3,560,587 A * | 2/1971 | Borst | 585/714 |
| 3,657,109 A | 4/1972 | Beyaert | 208/80 |
| 3,787,518 A | 1/1974 | Anderson | 260/683.45 |
| 3,830,865 A | 8/1974 | Anderson | 260/671 R |
| 3,846,505 A | 11/1974 | Anderson | 260/683.45 |
| 3,867,473 A | 2/1975 | Anderson | 260/683.45 |
| 3,911,043 A | 10/1975 | Anderson | 260/683.45 |
| RE29,084 E | 12/1976 | Anderson et al. | 260/683.41 |
| 4,220,806 A | 9/1980 | Mikulicz et al. | 585/716 |
| 4,429,173 A | 1/1984 | Hutson, Jr. et al. | 585/331 |
| 4,579,998 A | 4/1986 | Hutson, Jr. | 585/716 |
| 5,382,744 A | 1/1995 | Abbott et al. | 585/709 |
| 5,583,275 A | 12/1996 | Kranz et al. | 585/709 |
| 6,426,441 B1 * | 7/2002 | Randolph et al. | 585/712 |
| 6,429,349 B1 | 8/2002 | Grimes et al. | 585/719 |

* cited by examiner

*Primary Examiner*—Thuan Dlnh Dang
(74) *Attorney, Agent, or Firm*—James C Paschall

(57) ABSTRACT

A system and/or process for increasing the isobutane to olefin ratio in an alkylation process/system is disclosed. The system and/or process includes provisions for charging a portion of the settler effluent as a feed to at least one reaction zone downflow from the first reaction zone of a multi-zone alkylation reactor along with a portion of the olefin feed to the multi-zone alkylation reactor.

8 Claims, 2 Drawing Sheets

ALKYLATION PROCESS WITH SETTLER EFFLUENT RECYCLE

The present invention relates to a method and/or system for the alkylation of an olefin with an isoparaffin utilizing an acidic catalyst mixture. In another aspect, this invention relates to a method of increasing the isoparaffin to olefin ratio in the alkylation reactor section in order to reduce the amount of isopentane made in the reaction of isobutane with olefin.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the reaction mixture to separate the catalyst from the hydrocarbons, thereby forming a catalyst mixture phase and an alkylation reactor effluent. The alkylation reactor effluent is further separated, for example, by fractionation, to recover the separate product streams. Normally, the alkylation reactor effluent of the alkylation process contains hydrocarbons having five to ten carbon atoms per molecule. In order to have the highest quality gasoline blending stock, it is preferred for the alkylate hydrocarbons formed in the alkylation process to be highly branched and contain seven to nine carbon atoms per molecule.

It has long been known that increasing the isobutane to olefin ratio in an alkylation reactor is beneficial to alkylate product quality. Many alkylation unit operators run their downstream hydrocarbon fractionation sections at or near their full capacity, and thus, are constrained from recycling additional isobutane to the alkylation reactor section. Therefore, development of an improved process and/or system for increasing the isobutane to olefin ratio in an alkylation reactor without increasing the capacity load on the fractionation system would be a significant contribution to the art.

BRIEF SUMMARY OF THE INVENTION

It is, thus, an object of the present invention to provide an improved process and/or system for increasing the isobutane to olefin ratio in a multi-zone alkylation reactor.

A further object of this invention is to provide an improved process and/or system for increasing the isobutane to olefin ratio in a multi-zone alkylation reactor wherein the capacity load on the settler effluent fractionation section is not significantly increased.

A yet further object of the present invention is to provide an improved process and/or system for increasing the isobutane to olefin ratio in a multi-zone alkylation reactor wherein a portion of the settler effluent is charged to at least one alkylation reaction zone down-flow from the first alkylation reaction zone.

In accordance with a first embodiment of the present invention, a process for alkylating isobutane with an olefin is provided including the following steps:

a) mixing i) a first isobutane-containing feed stream selected from the group consisting of a portion of a fresh isobutane stream, a portion of a recycle isobutane stream, and combinations thereof; and ii) a first olefin stream with an alkylation catalyst stream in a first reaction zone, to thereby form a first reaction zone effluent;

b) passing the first reaction zone effluent to a second reaction zone for mixture with i) a second isobutane-containing feed stream selected from the group consisting of a portion of the fresh isobutane stream, a portion of the recycle isobutane stream, a portion of a settler effluent stream, and combinations of any two or more thereof; and ii) a second olefin stream to thereby form a second reaction zone effluent;

c) alternatively:

I) passing the second reaction zone effluent to a settler vessel for separation into a hydrocarbon phase and an acid phase; or II) 1) passing the second reaction zone effluent to a third reaction zone for mixture with i) a third isobutane-containing feed stream selected from the group consisting of a portion of the fresh isobutane stream, a portion of the recycle isobutane stream, a portion of the settler effluent stream, and combinations of any two or more thereof; and ii) a third olefin stream to thereby form a third reaction zone effluent; and 2) passing the third reaction zone effluent to a settler vessel for separation into a hydrocarbon phase and an acid phase; and d) removing at least a portion of the hydrocarbon phase to thereby form the settler effluent stream; and e) removing isobutane from the remainder of the hydrocarbon phase to thereby form the recycle isobutane stream.

In accordance with a second embodiment of the present invention, a system useful for alkylating isobutane with an olefin is provided including the following:

a multi-zone alkylation reactor comprising a first reaction zone and a second reaction zone, operably related to each other such that a first reaction zone effluent passes to the second reaction zone from the first reaction zone;

first conduit means operably related in fluid flow communication to the first reaction zone for introducing a first olefin stream into the first reaction zone;

second conduit means operably related in fluid flow communication to the first reaction zone for introducing a portion of a fresh isobutane stream into the first reaction zone;

third conduit means operably related in fluid flow communication to the second reaction zone for introducing a second olefin stream into the second reaction zone;

fourth conduit means operably related in fluid flow communication to the second reaction zone and to the second conduit means for introducing a portion of the fresh isobutane stream into the second reaction zone;

fifth conduit means operably related in fluid flow communication to the second reaction zone and operably related to a settler vessel for transport of a second reaction zone effluent to the settler vessel for separation into a hydrocarbon phase and an acid phase;

sixth conduit means operably related in fluid flow communication to the settler vessel and to the second reaction zone for transporting a portion of the hydrocarbon phase as a settler effluent stream from the settler vessel to the second reaction zone; and seventh conduit means operably related in fluid flow communication to the settler vessel and to the first reaction zone for transporting at least a portion of the acid phase as an alkylation catalyst stream to the first reaction zone.

In accordance with a third embodiment of the present invention, a system useful for alkylating isobutane with an olefin is provided including the following:

a multi-zone alkylation reactor comprising a first reaction zone, a second reaction zone, and a third reaction zone operably related to each other such that a first reaction zone effluent passes to the second reaction zone from the first reaction zone and such that a second reaction zone effluent passes to the third reaction zone from the second reaction zone;

first conduit means operably related in fluid flow communication to the first reaction zone for introducing a first olefin stream into the first reaction zone;

second conduit means operably related in fluid flow communication to the first reaction zone for introducing a portion of a fresh isobutane stream into the first reaction zone;

third conduit means operably related in fluid flow communication to the second reaction zone for introducing a second olefin stream into the second reaction zone;

fourth conduit means operably related in fluid flow communication to the second reaction zone and to the second conduit means for introducing a portion of the fresh isobutane stream into the second reaction zone;

fifth conduit means operably related in fluid flow communication to the third reaction zone for introducing a third olefin stream into the third reaction zone;

sixth conduit means operably related in fluid flow communication to the third reaction zone and to the second conduit means for introducing a portion of the fresh isobutane stream into the third reaction zone;

seventh conduit means operably related in fluid flow communication to the third reaction zone and operably related to a settler vessel for transport of a third reaction zone effluent to the settler vessel for separation into a hydrocarbon phase and an acid phase;

eighth conduit means operably related in fluid flow communication to the settler vessel and to the second reaction zone for transporting a portion of the hydrocarbon phase as a settler effluent stream from the settler vessel to the second reaction zone; and ninth conduit means operably related in fluid flow communication to the settler vessel and to the first reaction zone for transporting at least a portion of the acid phase as an alkylation catalyst stream to the first reaction zone.

DETAILED DESCRIPTION OF THE INVENTION

Figure 1:
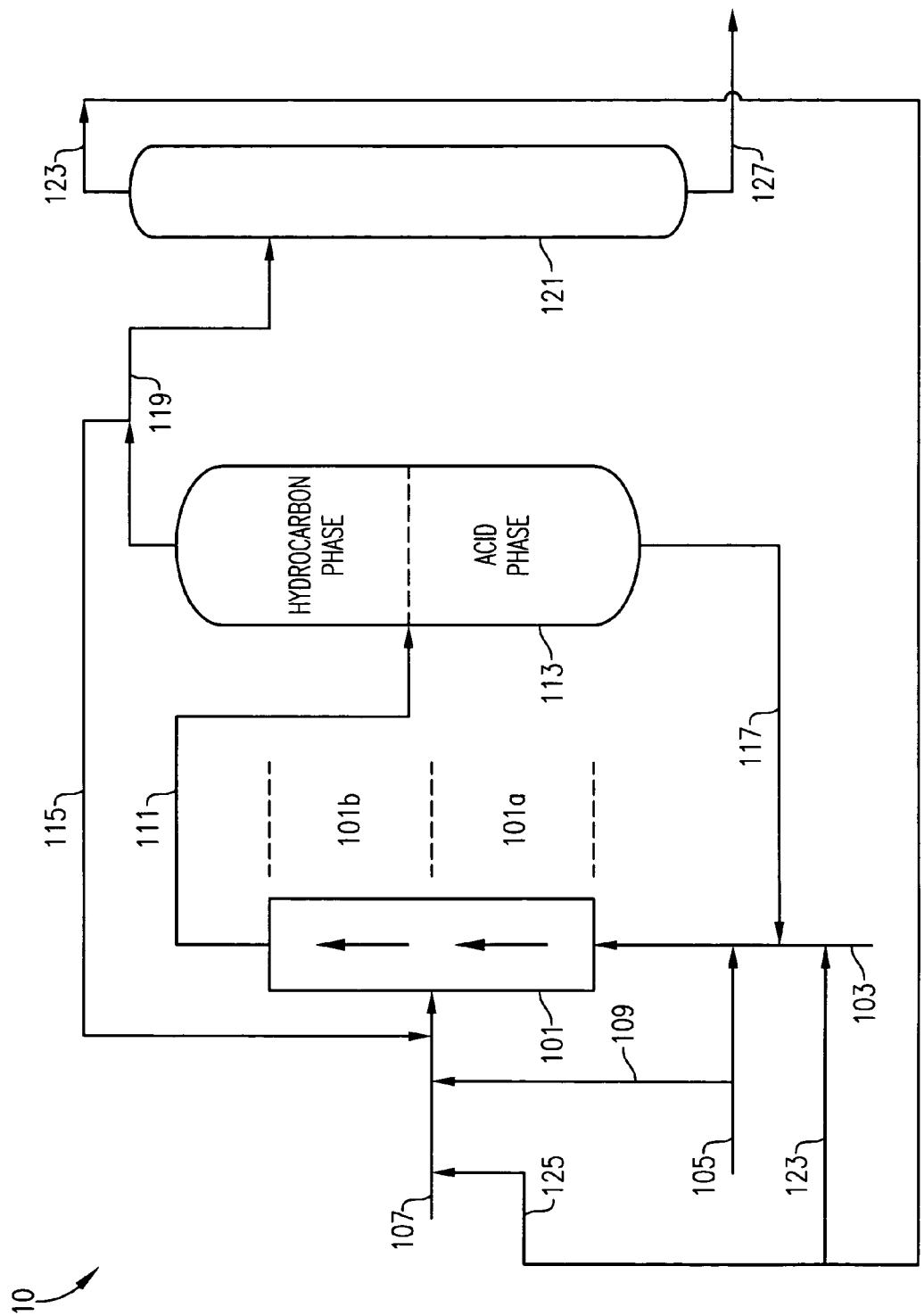
FIGS. 1 and 2 are simplified schematic flow diagrams presenting different embodiments of the invention process.

The first, second and third olefin streams suitable for use in the present invention each separately comprise, consist of, or consist essentially of a $C_4$ olefin selected from the group consisting of isobutene, butene-1, butene-2, and combinations thereof. Such first, second and third olefin streams can separately further comprise, consist of, or consist essentially of propene and/or an olefin containing five carbon atoms per molecule.

The fresh isobutane stream suitable for use in the present invention comprises at least about 60 wt. %, more preferably at least about 70 wt. %, and most preferably at least about 90 wt. % isobutane. The recycle isobutane stream suitable for use in the present invention comprises at least about 60 wt. %, more preferably at least about 80 wt. %, and most preferably at least about 85 wt. % isobutane. The settler effluent stream of the present invention typically comprises at least about 40 wt. %, more typically at least about 50 wt. % and most typically at least about 60 wt. % isobutane, and also typically comprises at least about 0.3 wt. %, more typically at least about 0.6 wt. %, and most typically at least about 1.0 wt. % isopentane.

The alkylation catalyst stream suitable for use in the present invention is selected from the group consisting of sulfuric acid and hydrofluoric acid. The alkylation catalyst stream can also further comprise a volatility reducing additive. The alkylation catalyst stream can also still further comprise water and acid soluble oil, which is a by-product of the alkylation process.

The volatility reducing additive can be any compound effective in reducing the volatility of a mixture resulting from the addition of the volatility reducing additive to the acid. More particularly, the volatility reducing additive can be a compound selected from the group consisting of sulfone, ammonia, methylamines, ethylamines, propylamines, butylamines, pentylamines, pyridine, alkylpyridines, picoline, melamine, hexamethylene-tetramine and the like.

The sulfones suitable for use in this invention are the sulfones of the general formula

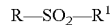

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfolane.

Preferably, the alkylation catalyst stream comprises, consists of, or consists essentially of hydrofluoric acid, more preferably comprises, consists of, or consists essentially of hydrofluoric acid and a volatility reducing additive, and most preferably comprises, consists of, or consists essentially of hydrofluoric acid and sulfone.

According to the first embodiment (alternative I of step c) and the second embodiment of the present invention, and referring to FIG. 1, an alkylation process system 10 is depicted which can comprise, consist of, or consist essentially of the following steps/components.

Providing a multi-zone alkylation reactor 101 defining a first reaction zone 101a and a second reaction zone 101b. Such first reaction zone 101a and second reaction zone 101b are operably related to each other such that a first reaction zone effluent passes to second reaction zone 101b from the first reaction zone 101a. The multi-zone alkylation reactor 101 is operably related in fluid flow communication to a conduit 103 providing first conduit means for introducing a first olefin stream into first reaction zone 101a. Conduit 103 is operably related in fluid flow communication with a conduit 105 providing second conduit means for receiving a fresh isobutane stream and for introducing a portion of the fresh isobutane stream into first reaction zone 101a. Multi-zone alkylation reactor 101 is operably related in fluid flow communication to a conduit 107 providing third conduit means for introducing a second olefin stream into a second reaction zone 101b. Conduits 105 and 107 are operably related in fluid flow communication via a conduit 109 providing fourth conduit means for introducing a portion of the fresh isobutane stream into second reaction zone 101b via conduit 107. Multi-zone alkylation reactor 101 is operably related in fluid flow communication via a conduit 111 to a settler vessel 113 and conduit 111 provides fifth conduit means for transport of a second reaction zone effluent from second reaction zone 101b to settler vessel 113 for separation into a hydrocarbon phase and an acid phase. Settler vessel 113 is operably related in fluid flow communication via conduit 115 to second reaction zone 101b and conduit 115 provides sixth conduit means for removing at least a portion of the hydrocarbon phase as a settler effluent stream from settler vessel 113 and for transporting at least a portion of the settler effluent stream to second reaction zone 101b.

Settler vessel 113 is operably related in fluid flow communication via a conduit 117 to conduit 103 and conduit 117 provides seventh conduit means for transporting at least a portion of the acid phase as an alkylation catalyst stream to first reaction zone 101a via conduit 103.

Optionally, conduit 115 is operably related in fluid flow communication via a conduit 119 to a fractionator 121 and conduit 119 provides eighth conduit means for transporting a portion of the settler effluent stream from conduit 115 to fractionator 121.

Optionally, fractionator 121 is operably related in fluid flow communication via conduit 123 to conduit 103 and conduit 123 provides ninth conduit means for removing a recycle isobutane stream from fractionator 121 and for transporting at least a portion of the recycle isobutane stream to first reaction zone 101a via conduit 103.

Conduit 123 is optionally operably related in fluid flow communication via conduit 125 to conduit 107 and conduit 125 provides tenth conduit means for transporting at least a portion of the recycle isobutane stream to second reaction zone 101b via conduit 107.

Fractionator 121 is operably related in fluid flow communication to a conduit 127 providing eleventh conduit means for removing an alkylate product stream from fractionator 121.

It being understood that FIG. 1 represents an embodiment of the invention and that generally the isobutane fed to reaction zone 101b via conduit 107 comprises a second isobutane-containing feed stream selected from the group consisting of the fresh isobutane stream, the recycle isobutane stream, the settler effluent stream, and combinations thereof. By no means is FIG. 1 to be construed to limit the invention such that portions of each of the fresh isobutane stream, the recycle isobutane stream and the settler effluent stream must be fed to the second reaction zone 101b.

Figure 2:
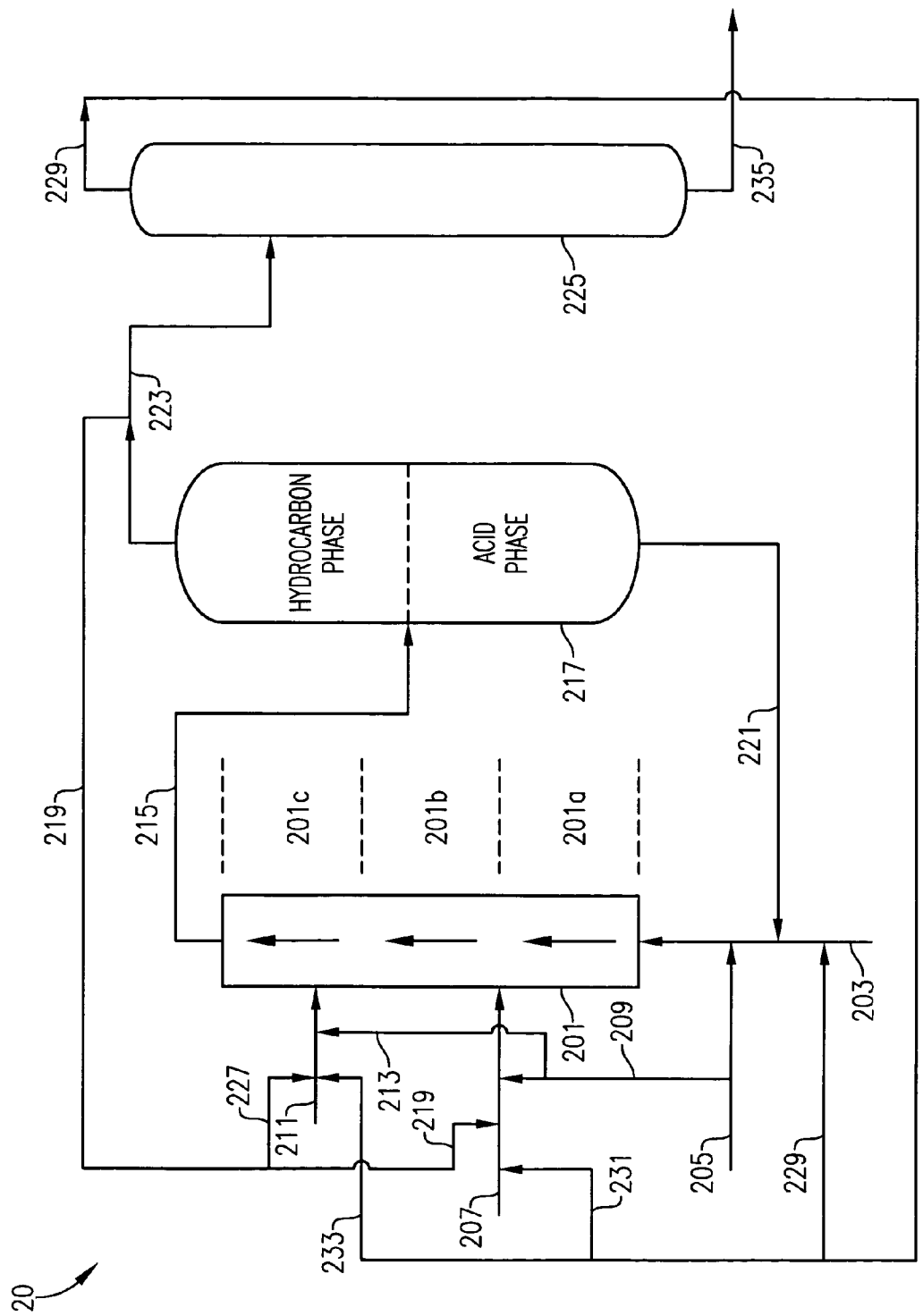

According to the first embodiment (alternative II of step c) and the third embodiment of the present invention, and referring to FIG. 2, an alkylation process system 20 is depicted which can comprise, consist of, or consist essentially of the following steps.

Providing a multi-zone alkylation reactor 201 defining a first reaction zone 201a, a second reaction zone 201b, and a third reaction zone 201c. Such first reaction zone 201a and second reaction zone 201b are operably related to each other such that a first reaction zone effluent passes to second reaction zone 201b from first reaction zone 201a. Such second reaction zone 201b and third reaction zone 201c are operably related to each other such that the second reaction zone effluent passes to third reaction zone 201c from second reaction zone 201b. The multi-zone alkylation reactor 201 is operably related in fluid flow communication to a conduit 203 providing first conduit means for introducing a first olefin stream into first reaction zone 201a. Conduit 203 is operably related in fluid flow communication with a conduit 205 providing second conduit means for receiving a fresh isobutane stream and for introducing a portion of the fresh isobutane stream into first reaction zone 201a. Multi-zone alkylation reactor 201 is operably related in fluid flow communication to a conduit 207 providing third conduit means for introducing a second olefin stream into a second reaction zone 201b. Conduits 205 and 207 are operably related in fluid flow communication via a conduit 209 providing fourth conduit means for introducing a portion of the fresh isobutane stream into second reaction zone 201b via conduit 207. Multi-zone alkylation reactor 201 is operably related in fluid flow communication to a conduit 211 providing fifth conduit means for introducing a third olefin stream into third reaction zone 201c.

Conduit 209 is operably related in fluid flow communication via conduit 213 to conduit 211 and conduit 213 provides sixth conduit means for introducing a portion of the fresh isobutane steam into third reaction zone 201c. Multi-zone alkylation reactor 201 is operably related in fluid flow communication via a conduit 215 to a settler vessel 217 and conduit 215 provides seventh conduit means for transport of a third reaction zone effluent from third reaction zone 201c to settler vessel 217 for separation into a hydrocarbon phase and an acid phase. Settler vessel 217 is operably related in fluid flow communication via conduit 219 to second reaction zone 201b and conduit 219 provides eighth conduit means for removing at least a portion of the hydrocarbon phase as a settler effluent stream from settler vessel 217 and for transporting at least a portion of the settler effluent stream to second reaction zone 201b.

Settler vessel 217 is operably related in fluid flow communication via a conduit 221 to conduit 203 and conduit 221 provides ninth conduit means for transporting at least a portion of the acid phase as an alkylation catalyst stream to first reaction zone 201a via conduit 203.

Optionally, conduit 219 is operably related via conduit 223 to a fractionator 225 and conduit 223 provides tenth conduit means for transporting a portion of the settler effluent stream from conduit 219 to fractionator 225.

Conduit 219 is optionally operably related in fluid flow communication via a conduit 227 to conduit 211 and conduit 227 provides eleventh conduit means for transporting a portion of the settler effluent stream from conduit 223 to third reaction zone 201c via conduit 211.

Fractionator 225 is optionally operably related in fluid flow communication via conduit 229 to conduit 203 and conduit 229 provides twelfth conduit means for removing a recycle isobutane stream from fractionator 225 and for transporting at least a portion of the recycle isobutane stream to first reaction zone 201a via conduit 203.

Conduit 229 is optionally operably related in fluid flow communication via conduit 231 to conduit 207 and conduit 231 provides thirteenth conduit means for transporting at least a portion of the recycle isobutane stream to second reaction zone 201b via conduit 207. Conduit 231 is also optionally operably related in fluid flow communication via conduit 233 to conduit 211 and conduit 233 provides fourteenth conduit means for transport of a portion of the recycle isobutane stream to third reaction zone 201c via conduit 211.

Fractionator 225 is operably related in fluid flow communication to a conduit 235 providing fifteenth conduit means for removing an alkylate product stream from fractionator 225.

It being understood that FIG. 2 represents an embodiment of the invention and that generally the isobutane fed to reaction zone 201b via conduit 207 comprises a second isobutane-containing feed stream selected from the group consisting of the fresh isobutane stream, the recycle isobutane stream, the settler effluent stream, and combinations thereof. It also being understood that generally the isobutane fed to reaction zone 201c via conduit 211 comprises a third isobutane-containing feed stream selected from the group consisting of the fresh isobutane stream, the recycle isobutane stream, the settler effluent stream, and combinations thereof. By no means is FIG. 2 to be construed to limit the invention such that portions of each of the fresh isobutane stream, the recycle isobutane stream and the settler effluent stream must be fed to each of the reaction zones 201b and 201c.

EXAMPLE

The following example is presented to further illustrate the invention and is not to be construed as unduly limiting its scope.

The data presented in Tables 1 and 2 was generated via a computer simulation program of an HF alkylation unit. The Comparative Simulation A is for an HF alkylation unit which does not include charging at least a portion of a settler effluent stream to a reaction zone down flow from the first reaction zone. The Inventive Process Simulation B is for an HF alkylation unit which does include charging at least a portion of a settler effluent stream to a reaction zone downflow from the first reaction zone. For both simulations, the following parameters were used:

Temperature=about 90° F. Inlet; and
   about 98° F. Outlet

Catalyst:
   about 81 wt. % HF,
   about 4 wt. % ASO,
   about 2 wt. % $H_2O$, and
   about 10 wt. % sulfone (Additive)

TABLE 1

Comparative Simulation A
BASIS: 7.25 to 1 External Isobutane/Olefin Ratio
9.9 to 1 Internal Isobutane/Olefin Ratio in 1st Reaction Zone
5.5 to 1 Internal Isobutane/Olefin Ratio in 2nd Reaction Zone

|  | Zone 101A* Feed | | | Zone 101B Feed | | | | | |
| --- | --- | --- | --- | --- | --- | --- | --- | --- | --- |
|  | OLEFIN | OUTSIDE ISOBUTANE | RECYCLE ISOBUTANE | OLEFIN | OUTSIDE ISOBUTANE | SETTLER EFFLUENT | RECYCLE ISOBUTANE | PROPANE PRODUCT | AKLYLATE PRODUCT |
| Mass Flows lb/hr | 103* | 105 | 123 | 107 | 109 | 115 | 125 |  | 127 |
| ETHANE | 45.4 | 37.2 | 33.3 | 68.1 | 0.0 | 0.0 | 35.7 | 150.6 | 0.0 |
| PROPENE | 16,011.0 | 0.0 | 0.0 | 24,016.5 | 0.0 | 0.0 | 0.0 | 0.0 | 0.0 |
| PROPANE | 5,129.6 | 2,156.5 | 33,635.9 | 7,694.4 | 0.0 | 0.0 | 36,150.1 | 20,805.0 | 0.0 |
| I-BUTANE | 10,995.9 | 74,357.5 | 223,208.2 | 16,493.8 | 0.0 | 0.0 | 239,892.5 | 465.6 | 476.1 |
| I-BUTENE | 4,621.7 | 0.0 | 0.0 | 6,932.5 | 0.0 | 0.0 | 0.0 | 0.0 | 0.0 |
| 1-BUTENE | 3,217.1 | 0.0 | 0.0 | 4,825.6 | 0.0 | 0.0 | 0.0 | 0.0 | 0.0 |
| BUTANE | 1,684.6 | 6,677.1 | 19,343.6 | 2,526.8 | 0.0 | 0.0 | 20,789.5 | 4.6 | 10,878.1 |
| T-2-BUTENE | 4,307.1 | 0.0 | 0.0 | 6,460.6 | 0.0 | 0.0 | 0.0 | 0.0 | 0.0 |
| C-2-BUTENE | 2,453.6 | 0.0 | 0.0 | 3,680.3 | 0.0 | 0.0 | 0.0 | 0.0 | 0.0 |
| HF | 0.0 | 0.0 | 0.4 | 0.0 | 0.0 | 0.0 | 0.4 | 0.0 | 0.0 |
| 3M1-BUTENE | 0.0 | 0.0 | 0.0 | 0.0 | 0.0 | 0.0 | 0.0 | 0.0 | 0.0 |
| I-PENTANE | 1,738.5 | 717.6 | 4,653.7 | 2,607.8 | 0.0 | 0.0 | 5,001.6 | 0.0 | 15,982.3 |
| 1-PENTENE | 217.4 | 0.0 | 0.0 | 326.1 | 0.0 | 0.0 | 0.0 | 0.0 | 0.0 |
| 2M1-BUTENE | 0.0 | 0.0 | 0.0 | 0.0 | 0.0 | 0.0 | 0.0 | 0.0 | 0.0 |
| PENTANE | 45.9 | 94.2 | 55.9 | 68.9 | 0.0 | 0.0 | 60.1 | 0.0 | 220.1 |
| T-2-PENTENE | 0.0 | 0.0 | 0.0 | 0.0 | 0.0 | 0.0 | 0.0 | 0.0 | 0.0 |
| C-2-PENTENE | 0.0 | 0.0 | 0.0 | 0.0 | 0.0 | 0.0 | 0.0 | 0.0 | 0.0 |
| 2M2-BUTENE | 85.0 | 0.0 | 0.0 | 127.6 | 0.0 | 0.0 | 0.0 | 0.0 | 0.0 |
| 1,3 BUTADIENE | 137.0 | 0.0 | 0.0 | 205.4 | 0.0 | 0.0 | 0.0 | 0.0 | 0.0 |
| C6+ | 49.5 | 31.5 | 5,498.0 | 74.3 | 0.0 | 0.0 | 5,908.9 | 0.0 | 161,216.4 |
| ASO | 0.0 | 0.0 | 0.0 | 0.0 | 0.0 | 0.0 | 0.0 | 0.0 | 0.2 |
| ADDITIVE | 0.0 | 0.0 | 0.0 | 0.0 | 0.0 | 0.0 | 0.0 | 0.0 | 58.2 |
| TOTAL | 50,739.3 | 84,071.6 | 286,429.0 | 76,108.7 | 0.0 | 0.0 | 307,838.8 | 21,425.8 | 188,831.4 |

*Identifying numbers correspond to those in FIG. 1 and are presented here as an aid in reviewing this Table 1.

TABLE 2

Comparative Simulation B
BASIS: 7.25 to 1 External Isobutane/Olefin Ratio
13 to 1 Internal Isobutane/Olefin Ratio in 1st Reaction Zone
8.2 to 1 Internal Isobutane/Olefin Ratio in 2nd Reaction Zone

| | Zone 101A* Feed | | | Zone 101B Feed | | | | | |
|---|---|---|---|---|---|---|---|---|---|
| | OLEFIN | OUTSIDE ISOBUTANE | RECYCLE ISOBUTANE | OLEFIN | OUTSIDE ISOBUTANE | SETTLER EFFLUENT | RECYCLE ISOBUTANE | PROPANE PRODUCT | AKLYLATE PRODUCT |
| Mass Flows lb/hr | 103 | 105 | 123 | 107 | 109 | 115 | 125 | | 127 |
| ETHANE | 45.4 | 37.4 | 47.7 | 68.1 | 0.0 | 104.2 | 21.4 | 150.9 | 0.0 |
| PROPENE | 16,011.0 | 0.0 | 0.0 | 24,016.5 | 0.0 | 0.0 | 0.0 | 0.0 | 0.0 |
| PROPANE | 5,129.6 | 2,169.8 | 48,255.7 | 7,694.4 | 0.0 | 43,522.9 | 21,593.8 | 20,818.4 | 0.0 |
| I-BUTANE | 10,995.9 | 74,816.1 | 319,617.6 | 16,493.8 | 0.0 | 224,972.7 | 143,024.6 | 464.8 | 481.4 |
| I-BUTENE | 4,621.7 | 0.0 | 0.0 | 6,932.5 | 0.0 | 0.0 | 0.0 | 0.0 | 0.0 |
| 1-BUTENE | 3,217.1 | 0.0 | 0.0 | 4,825.6 | 0.0 | 0.0 | 0.0 | 0.0 | 0.0 |
| BUTANE | 1,684.6 | 6,718.3 | 27,749.6 | 2,526.8 | 0.0 | 24,524.0 | 12,417.6 | 4.6 | 10,919.3 |
| T-2-BUTENE | 4,307.1 | 0.0 | 0.0 | 6,460.6 | 0.0 | 0.0 | 0.0 | 0.0 | 0.0 |
| C-2-BUTENE | 2,453.6 | 0.0 | 0.0 | 3,680.3 | 0.0 | 0.0 | 0.0 | 0.0 | 0.0 |
| HF | 0.0 | 0.0 | 0.5 | 0.0 | 0.0 | 3,221.8 | 0.2 | 0.0 | 0.0 |
| 3M1-BUTENE | 0.0 | 0.0 | 0.0 | 0.0 | 0.0 | 0.0 | 0.0 | 0.0 | 0.0 |
| I-PENTANE | 1,738.5 | 722.0 | 6,676.3 | 2,607.8 | 0.0 | 10,254.8 | 2,987.6 | 0.0 | 12,060.1 |
| 1-PENTENE | 217.4 | 0.0 | 0.0 | 326.1 | 0.0 | 0.0 | 0.0 | 0.0 | 0.0 |
| 2M1-BUTENE | 0.0 | 0.0 | 0.0 | 0.0 | 0.0 | 0.0 | 0.0 | 0.0 | 0.0 |
| PENTANE | 45.9 | 94.8 | 80.2 | 68.9 | 0.0 | 162.1 | 35.9 | 0.0 | 220.8 |
| T-2-PENTENE | 0.0 | 0.0 | 0.0 | 0.0 | 0.0 | 0.0 | 0.0 | 0.0 | 0.0 |
| C-2-PENTENE | 0.0 | 0.0 | 0.0 | 0.0 | 0.0 | 0.0 | 0.0 | 0.0 | 0.0 |
| 2M2-BUTENE | 85.0 | 0.0 | 0.0 | 127.6 | 0.0 | 0.0 | 0.0 | 0.0 | 0.0 |
| 1,3 BUTADIENE | 137.0 | 0.0 | 0.0 | 205.4 | 0.0 | 0.0 | 0.0 | 0.0 | 0.0 |
| C6+ | 49.5 | 31.7 | 7,887.4 | 74.3 | 0.0 | 81,577.7 | 3,529.4 | 0.0 | 165,597.6 |
| ASO | 0.0 | 0.0 | 0.0 | 0.0 | 0.0 | 0.1 | 0.0 | 0.0 | 0.2 |
| ADDITIVE | 0.0 | 0.0 | 0.0 | 0.0 | 0.0 | 25.1 | 0.0 | 0.0 | 54.8 |
| TOTAL | 50,739.3 | 84,590.1 | 410,315.0 | 76,108.7 | 0.0 | 388,365.4 | 183,610.5 | 21,438.7 | 189,334.2 |

*Identifying numbers correspond to those in FIG. 1 and are presented here as an aid in reviewing this Table 2.

As can be seen from the simulation data in Tables 1 and 2, the inventive process, which includes recycling at least a portion of the settler effluent to the reaction system, produces/results in less isopentane overall and higher internal Isobutane/Olefin Ratios as compared to the Comparative process without the recycling of least a portion of the settler effluent to the reaction system.

The invention claimed is:

1. A process comprising:
   a) mixing i) a first isobutane-containing feed stream selected from the group consisting of a portion of a fresh isobutane stream, a portion of a recycle isobutane stream, and combinations thereof; and ii) a first olefin stream with an alkylation catalyst stream in a first reaction zone, to thereby form a first reaction zone effluent;
   b) passing said first reaction zone effluent to a second reaction zone for mixture with i) a second isobutane-containing feed stream selected from the group consisting of a portion of said fresh isobutane stream, a portion of said recycle isobutane stream, a portion of a settler effluent stream, and combinations of any two or more thereof; and ii) a second olefin stream to thereby form a second reaction zone effluent;
   c) alternatively:
      I) passing said second reaction zone effluent to a settler vessel for separation into a hydrocarbon phase comprising alkylate and isobutane and an acid phase; or
      II) 1) passing said second reaction zone effluent to a third reaction zone for mixture with i) a third isobutane-containing feed stream selected from the group consisting of a portion of said fresh isobutane stream, a portion of said recycle isobutane stream, a portion of said settler effluent stream, and combinations of any two or more thereof; and ii) a third olefin stream to thereby form a third reaction zone effluent; and 2) passing said third reaction zone effluent to a settler vessel for separation into a hydrocarbon phase comprising alkylate and isobutane and an acid phase; and
   d) removing at least a portion of said hydrocarbon phase to thereby form said settler effluent stream comprising alkylate and isobutane; and
   e) removing isobutane from the remainder of said hydrocarbon phase to thereby form said recycle isobutane stream; and wherein at least a portion of said settler effluent stream comprising alkylate and isobutane is mixed with at least one of:
      1) said first reaction zone effluent in said second reaction zone in step b), and
      2) said second reaction zone effluent in said third reaction zone in step c) II).

2. A process in accordance with claim 1 further comprising the step:
   f) removing at least a portion of said acid phase for use as said alkylation catalyst stream.

3. A process in accordance with claim 1 wherein said fresh isobutane stream comprises at least about 60 wt. % isobutane, said recycle isobutane stream comprises at least about 60 wt. % isobutane, and said settler effluent stream comprises at least about 40 wt. % isobutane.

4. A process in accordance with claim 1 wherein said first, second and third olefin streams each separately comprise a $C_4$ olefin selected from the group consisting of isobutene, butene-1, butene-2, and combinations thereof.

5. A process in accordance with claim 4 wherein each of said first, second and third olefin streams separately further comprise propene and an olefin containing five carbon atoms per molecule.

6. A process in accordance with claim 1 wherein said alkylation catalyst stream comprises an acid selected from the group consisting of sulfuric acid and hydrofluoric acid.

7. A process in accordance with claim 1 wherein said alkylation catalyst stream comprises hydrofluoric acid and a volatility reducing additive.

8. A process in accordance with claim 7 wherein said volatility reducing additive is sulfone.

* * * * *